United States Patent [19]

Peet et al.

[11] Patent Number: 4,485,106
[45] Date of Patent: Nov. 27, 1984

[54] SUBSTITUTED TETRAHYDROTETRAZOLO[5,1-a]PHTHALAZINES

[75] Inventors: Norton P. Peet; Shyam Sunder, both of Indianapolis, Ind.

[73] Assignee: The Dow Chemical Company, Midland, Mich.

[21] Appl. No.: 397,297

[22] Filed: Jul. 12, 1982

[51] Int. Cl.$^3$ ..................... A61K 31/50; C07D 487/04
[52] U.S. Cl. .................................. 424/250; 544/234; 260/243.3
[58] Field of Search ....................... 544/234; 424/250; 260/243.3

[56] References Cited

U.S. PATENT DOCUMENTS 4,391,806 7/1983 Alexander et al. ................. 544/234
4,391,807 7/1983 Alexander et al. ................. 544/234

FOREIGN PATENT DOCUMENTS 29130 5/1981 European Pat. Off. ............ 544/234

OTHER PUBLICATIONS

Stanovnik et al., *Synthesis* 1977, (7), p. 491.
Stanovnik et al., *Synthesis* 1978, (1), p. 65.
Twomey, *Proc. Roy. Ir. Acad.*, Sect. B 1974, 74 (4), 37.
Chem. Abstracts: vol. 86:171378j, Conalty et al.
Burger E. D., *Medicinal Chemistry* 3rd ed., Wiley-Interscience (1970), p. 76.
Karklina et al., Chem. Abstracts, vol. 81:37518y, (1974).

*Primary Examiner*—Paul M. Coughlan, Jr.
*Assistant Examiner*—William A. Teoli, Jr.
*Attorney, Agent, or Firm*—John J. Kolano; Gary D. Street; Richard G. Waterman

[57] ABSTRACT

Substituted tetrahydrotetrazolo[5,1-a]phthalazine compounds such as 6-methylamino-7,8,9,10-tetrahydrotetrazolo[5,1-a]phthalazine are prepared by reacting a 6-halo-7,8,9,10-tetrahydrotetrazolo[5,1-a]phthalazine with an appropriate amine. The compounds are useful as bronchodilators.

5 Claims, No Drawings

SUBSTITUTED TETRAHYDROTETRAZOLO[5,1-a]PHTHALAZINES

The present invention relates to tetrahydrotetrazolo[5,1-a]phthalazines having an amino substitutent at the 6-position. More particularly, it relates to compounds having the following general formula:

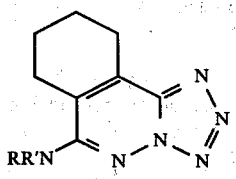

wherein —NRR' is (lower alkyl)amino, (lower alkyl)$_2$-amino, 1-pyrrolidinyl, 1-piperidinyl, methyl-1-piperidinyl, hexahydroazepin-1-yl, 4-methyl-1-piperazinyl, 4-methylhexahydro-1,4-diazepin-1-yl and 4-morpholinyl. The present invention further encompasses the pharmaceutically acceptable acid addition salts of the aforesaid amino compounds.

The lower alkyl groups referred to above contain 1 to 6 carbon atoms and can be exemplified by groups such as, methyl, ethyl, propyl, isopropyl, butyl, and hexyl.

Acid addition salts of the aforesaid compounds with pharmaceutically acceptable acids are equivalent to the above amines for the purposes of this invention. Illustrative of such salts are the salts with inorganic acids such as, for example, hydrochloric, hydrobromic, sulfuric, phosphoric and like acids; with organic carboxylic acids such as, for example, acetic, propionic, glycolic, lactic, pyruvic, malonic, succinic, fumaric, malic, tartaric, citric, ascorbic, maleic, hydroxymaleic and dihydroxymaleic, benzoic, phenylacetic, 4-aminobenzoic, 4-hydroxybenzoic, anthranilic, cinnamic, salicylic, 4-aminosalicylic, 2-phenoxybenzoic, 2-acetoxybenzoic, mandelic and like acids; and with organic sulfonic acids such as methanesulfonic acid and p-toluenesulfonic acid.

Examples of compounds encompassed by the present invention are the following:
6-Ethylamino-7,8,9,10-tetrahydrotetrazolo[5,1-a]phthalazine.
6-Diethylamino-7,8,9,10-tetrahydrotetrazolo[5,1-a]phthalazine.
6-(1-Piperidinyl)-7,8,9,10-tetrahydrotetrazolo[5,1-a]phthalazine.
6-(4-Methyl-1-piperidinyl)-7,8,9,10-tetrahydrotetrazolo[5,1-a]phthalazine.
6-(Hexahydroazepin-1-yl)-7,8,9,10-tetrahydrotetrazolo[5,1-a]phthalazine.
6-(4-Morpholinyl)-7,8,9,10-tetrahydrotetrazolo[5,1-a]phthalazine.

The substituted tetrahydrotetrazolo[5,1-a]phthalazine compounds as described above are bronchodilators and are thus useful for the treatment of bronchial disorders such as bronchial asthma. The present invention is further directed to a method of effecting bronchodilation.

In practicing the method of this invention, an effective bronchodilating amount of 1 or more substituted tetrahydrotetrazolo[5,1-a]phthalazine of this invention is administered internally to a mammal in need thereof by a route effective to bring the compound into contact with the bronchial and tracheal tissues of the mammal. Administration can be carried out either by a parenteral route, such as by intravenous, intraperitoneal or intramuscular injection, or by introduction into the gastrointestinal tract via oral or rectal administration, for example, in order to bring about such contact via the blood stream, or by intratracheal administration, by inhalation of a solution in the form of a spray, for example.

The effective bronchodilating amount of the compound, that is, the amount sufficient to inhibit or alleviate bronchial spasm, depends on various factors such as the size, type and age of the animal to be treated, the particular compound or pharmacologically-acceptable salt employed, the route and frequency of administration, the severity of any spasm and the causative agent involved, and the time of administration. In particular cases, the dosage to be administered can be ascertained by conventional range finding techniques, for example, by observing the bronchodilator activity produced at different dosage rates. More specifically, the compounds can be administered at dosage rates ranging from about 1 to about 100 milligrams of substituted tetrahydrotetrazolo[5,1-a]phthalazine compound per kilogram of animal body weight with other ranges being from about 1 to about 10 or from 1 to about 3 milligrams per kilogram. It is generally desirable to administer individual dosages at the lowest amount which provides the desired protection from bronchial spasm consonant with a convenient dosing schedule. Dosage units adaptable to oral administration such as tablets, capsules, lozenges, elixirs, syrups and the like are generally preferred and the active compound can be formulated in conventional time release capsule or tablet formulations although injectable compositions or sprays and aerosols for inhalation are preferred when rapid action is desired.

In practicing the method of this invention, the active ingredient is preferably incorporated in a composition comprising a pharmaceutical carrier and from about 5 to about 90 percent by weight of the substituted tetrahydrotetrazolo[5,1-a]phthalazine compound or a pharmaceutically-acceptable salt thereof. The term "pharmaceutical carrier" refers to known pharmaceutical excipients useful in formulating pharmaceutically active compounds for internal administration to animals, and which are substantially non-toxic and non-sensitizing under conditions of use. The compositions can be prepared by known techniques for the preparation of tablets, capsules, lozenges, troches, suppositories, elixirs, syrups, emulsions, dispersions, wettable and effervescent powders, sterile injectable compositions and solutions for sprays, and can contain suitable excipients known to be useful in the preparation of the particular type of composition desired. Suitable pharmaceutical carriers and formulation techniques are found in standard texts, such as Remington's Pharmaceutical Sciences, Mack Publishing Company, Easton, Pa.

In evaluating bronchodilator activity, test compounds were administered to guinea pigs by intraperitoneal injection or orally and the guinea pigs were challenged by exposure to a histamine aerosol at periods ranging from 30 minutes to 4 hours later. Untreated animals collapsed when exposed to the histamine aerosol. In these operations, the animals were observed and collapse times were recorded. The collapse times observed were then compared statistically with control animals treated with water alone with the control group usually being a long-term cumulative control. When tested by the above procedure, the compounds of the present invention were found to produce a bronchodilating effect.

The compounds of the present invention are conveniently prepared by the reaction of a 6-halo-7,8,9,10-tetrahydrotetrazolo[5,1-a]phthalazine with an appropriate amine. The 6-halo substituent is preferably chlorine although it can also be bromine. This 6-halo compound is reacted with an excess of the amine in an inert solvent. More specifically, the reaction is carried out at the boiling temperature under reflux or at about 60° C. to 110° C. using an excess of the base or an inert organic solvent such as methanol, ethanol or 2-propanol as a medium. The product is recovered by conventional procedures such as concentration under reduced pressure.

The starting material in the above procedure is obtained by reaction of an appropriate 1-halo-4-hydrazino-5,6,7,8-tetrahydrophthalazine with nitrous acid under appropriate reaction conditions.

The following examples are presented to illustrate the present invention but they should not be construed as limiting it in any way.

EXAMPLE 1

To a suspension of 9.9 g of 1-chloro-4-hydrazino-5,6,7,8-tetrahydrophthalazine in 35 ml of aqueous 12% acetic acid was added a solution of 3.5 g of sodium nitrite in 30 ml of water. The mixture was kept at room temperature (about 22°-25° C.) for about 20 minutes. The solid present was then separated by filtration, air dried and recrystallized to give 6-chloro-7,8,9,10-tetrahydrotetrazolo[5,1-a]phthalazine melting at about 109°-110° C.

EXAMPLE 2

A mixture of 6.0 g of 6-chloro-7,8,9,10-tetrahydrotetrazolo[5,1-a]phthalazine and 125 ml of 40% aqueous methylamine in 15 ml of methanol was heated under reflux for 3 hours. The reaction mixture was then cooled and the crystalline solid present was separated by filtration. It was recrystallized from a mixture of dimethylsulfoxide and water to give 6-methylamino-7,8,9,10-tetrahydrotetrazolo[5,1-a]phthalazine melting at about 318° C.

EXAMPLE 3

A mixture was prepared from 6 g of 6-chloro-7,8,9,10-tetrahydrotetrazolo[5,1-a]phthalazine, 150 ml of methanol and 125 ml of 40% aqueous dimethylamine. This mixture was heated at reflux for 3 hours and then cooled. The precipitate which formed was separated by filtration and partitioned between methylene chloride and water. The organic layer was separated, dried over sodium sulfate, and concentrated to leave a residual solid. This was recrystallized from ethanol to give 6-dimethylamino-7,8,9,10-tetrahydrotetrazolo[5,1-a]phthalazine melting at about 239°-240° C.

EXAMPLE 4

A mixture of 6 g of 6-chloro-7,8,9,10-tetrahydrotetrazolo[5,1-a]phthalazine, 150 ml of methanol and excess pyrrolidone was heated on a boiling-water steam bath for 10 minutes and cooled. The solid which formed was separated by filtration, washed with water and recrystallized from a mixture of dimethylsulfoxide and water to give 6-(1-pyrrolidinyl)-7,8,9,10-tetrahydrotetrazolo[5,1-a]phthalazine melting at about 272°-273° C.

EXAMPLE 5

The general procedures of Example 2 or 3 were repeated using 6-chloro-7,8,9,10-tetrahydrotetrazolo[5,1-a]phthalazine and 4-methylpiperazine or 4-methylhexahydro-1,4-diazepine. In both cases, the products obtained were then dissolved in ethyl acetate and mixed with a solution of hydrogen chloride in diethyl ether. The hydrochloride salt precipitated and was separated by filtration. The specific compounds thus obtained were:

6-(4-Methyl-1-piperazinyl)-7,8,9,10-tetrahydrotetrazolo[5,1-a]phthalazine melting at about 192°-193° C. after recrystallization from a mixture of benzene and hexane.

6-(4-Methyl-1-piperazinyl)-7,8,9,10-tetrahydrotetrazolo[5,1-a]phthalazine hydrochloride melting at about 265°-266° C. after recrystallization from a mixture of ethanol and ether.

6-(4-Methylhexahydro-1,4-diazepin-1-yl)-7,8,9,10-tetrahydrotetrazolo[5,1-a]phthalazine melting at about 160°-161° C. after recrystallization from ethanol.

6-(4-Methylhexahydro-1,4-diazepin-1-yl)-7,8,9,10-tetrahydrotetrazolo[5,1-a]phthalazine hydrochloride melting at about 255°-256° C. after recrystallization from ethanol.

What is claimed is:

1. A compound of the formula:

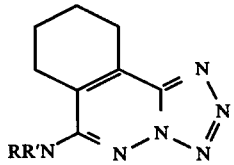

wherein —NRR' is (lower alkyl)amino, di(lower alkyl)amino, 1-pyrrolidinyl, 1-piperidinyl, methyl-1-piperidinyl, hexahydroazepin-1-yl, 4-methyl-1-piperazinyl and 4-methylhexahydro-1,4-diazepin-1-yl; and the pharmaceutically acceptable acid addition salts of said compound.

2. A compound according to claim 1 which is 6-(1-pyrrolidinyl)-7,8,9,10-tetrahydrotetrazolo[5,1-a]phthalazine.

3. A compound according to claim 1 which is 6-(4-methyl-1-piperazinyl)-7,8,9,10-tetrahydrotetrazolo[5,1-a]phthalazine.

4. A compound according to claim 1 which is 6-(4-methylhexahydro-1,4-diazepin-1-yl)-7,8,9,10-tetrahydrotetrazolo[5,1-a]phthalazine.

5. A method of producing bronchodilation which comprises administering to a mammal in need thereof an effective amount of a compound of the formula

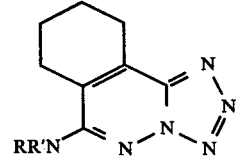

wherein —NRR' is (lower alkyl)amino, di(lower alkyl)amino, 1-pyrrolidinyl, 1-piperidinyl, methyl-1-piperidinyl, hexahydroazepin-1-yl, 4-methyl-1-piperazinyl and 4-methylhexahydro-1,4-diazepin-1-yl; and the pharmaceutically acceptable acid addition salts of said compound.

* * * * *